United States Patent [19]

Dror

[11] 4,187,845

[45] Feb. 12, 1980

[54] APPARATUS FOR FEEDING ANESTHETIC AND/OR LIFE SUSTAINING GASES DURING A SURGICAL PROCEDURE

[76] Inventor: Leon L. Dror, 922 W. Culver St., Phoenix, Ariz. 85007

[21] Appl. No.: 923,899

[22] Filed: Jul. 12, 1978

[51] Int. Cl.² .................................................. A61M 17/00
[52] U.S. Cl. .................................... 128/205.13; 128/273; 417/472; 417/384; 417/234; 417/544; 222/179; 222/628; 222/209
[58] Field of Search ............. 128/145.6, 142 R, 142.3, 128/142.4, 145 R, 145.5, 145.6, 145.7, 145.8, 147, 185, 195, 202, 203, 204, 205, 273, 172, 191 R, 198, 209, 140 R, 226, 231, 232; 222/179, 628, 209; 417/472, 473, 384, 389, 234, 235, 236, 237, 544

[56] References Cited

U.S. PATENT DOCUMENTS

| 591,052 | 10/1897 | McGregor | 128/142 R |
| 1,802,601 | 4/1931 | Heidbrink | 128/203 |
| 2,436,030 | 2/1948 | Abbott | 222/179 |
| 3,120,192 | 2/1964 | Winchell | 417/472 X |
| 3,613,677 | 10/1971 | Blasko | 128/145.6 |

FOREIGN PATENT DOCUMENTS

| 251448 | of 1912 | Fed. Rep. of Germany | 417/473 |
| 438980 | 11/1935 | United Kingdom | 128/142.3 |

Primary Examiner—Henry J. Recla
Attorney, Agent, or Firm—Warren F. B. Lindsley

[57] ABSTRACT

A mechanically operable bellows for feeding anesthetic and/or life sustaining gases to a patient during a surgical procedure.

6 Claims, 8 Drawing Figures

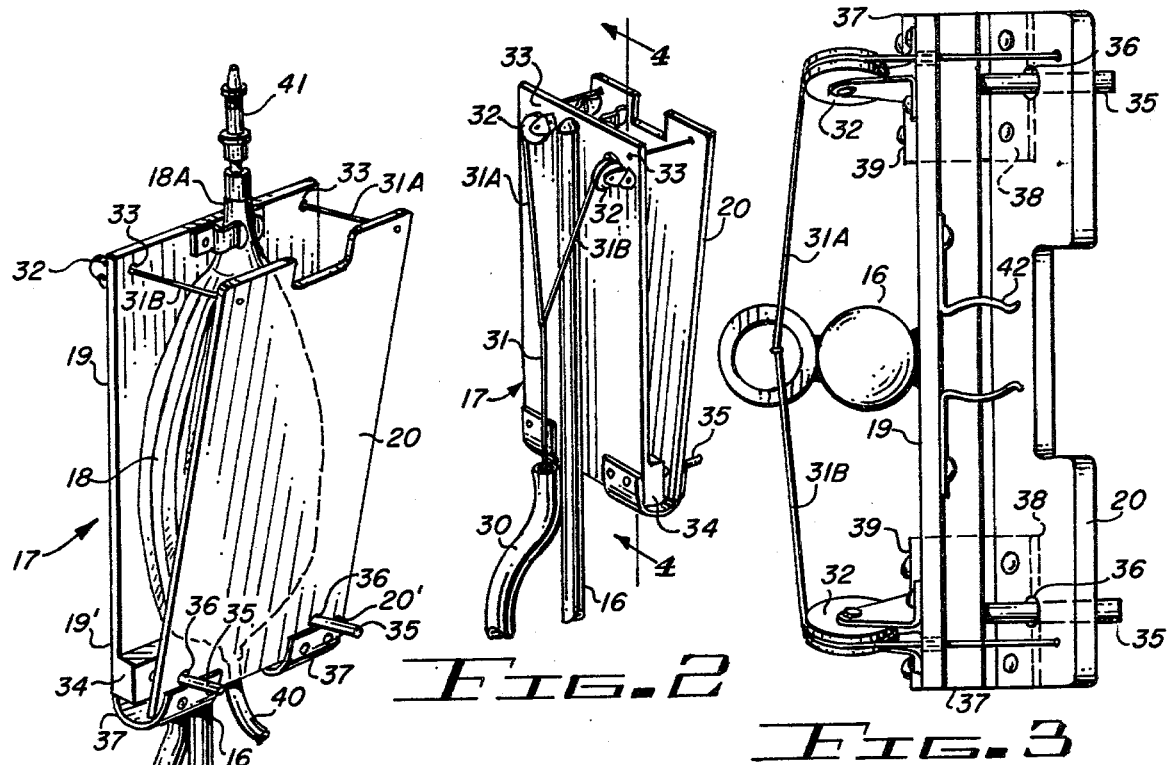
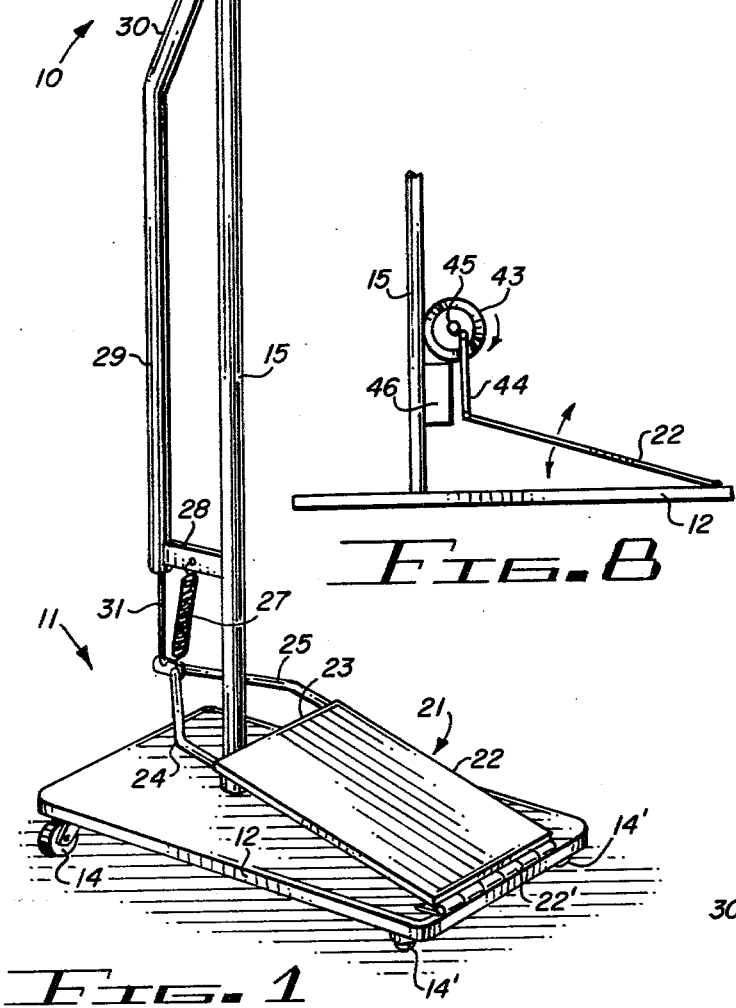
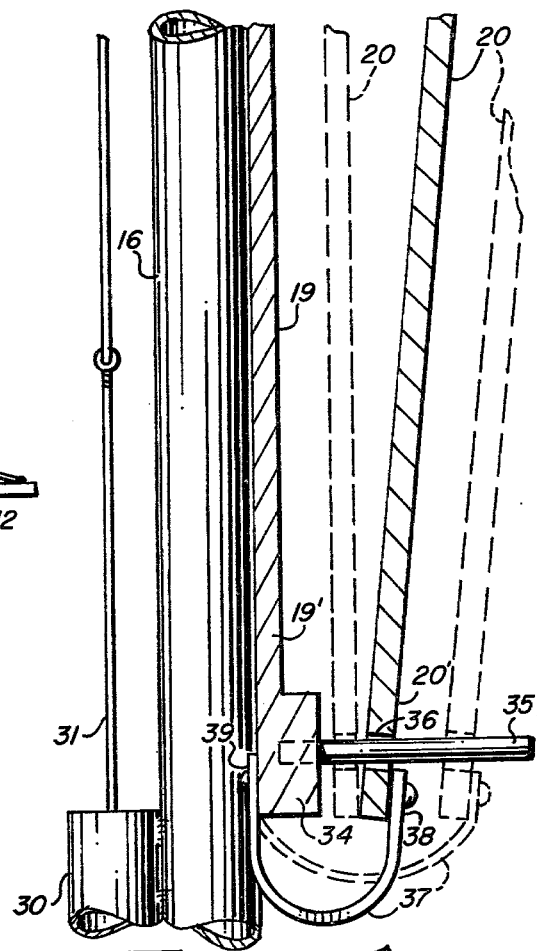

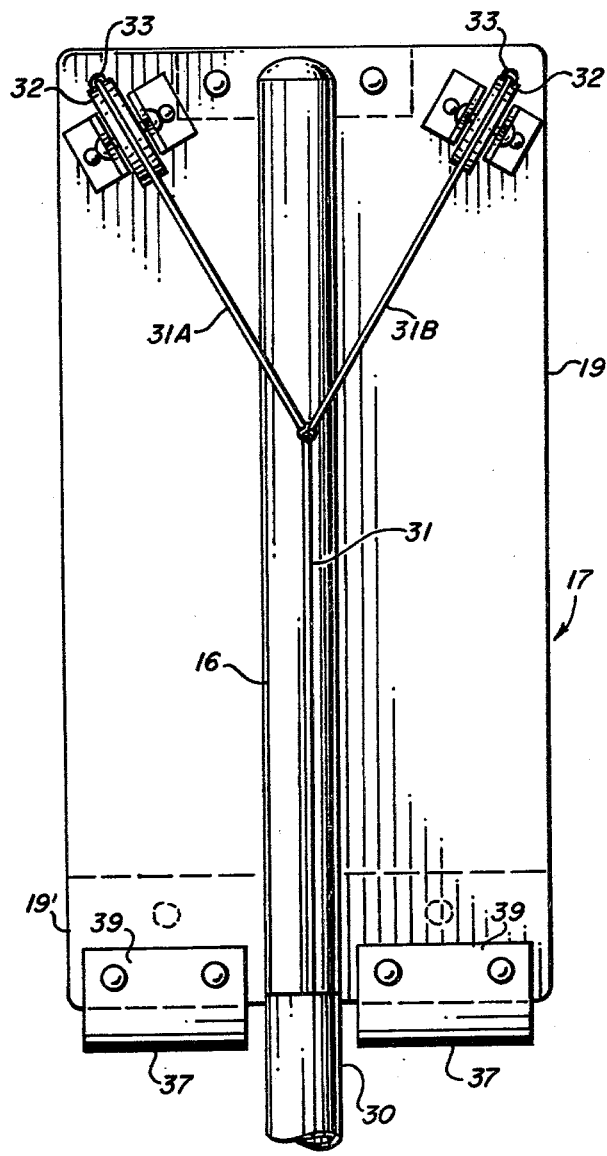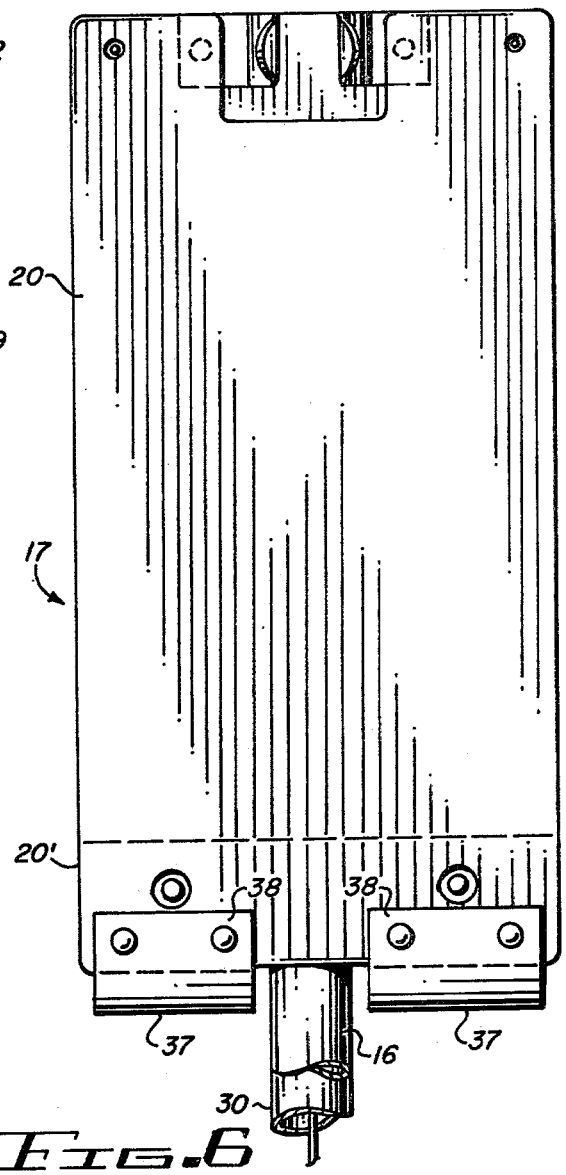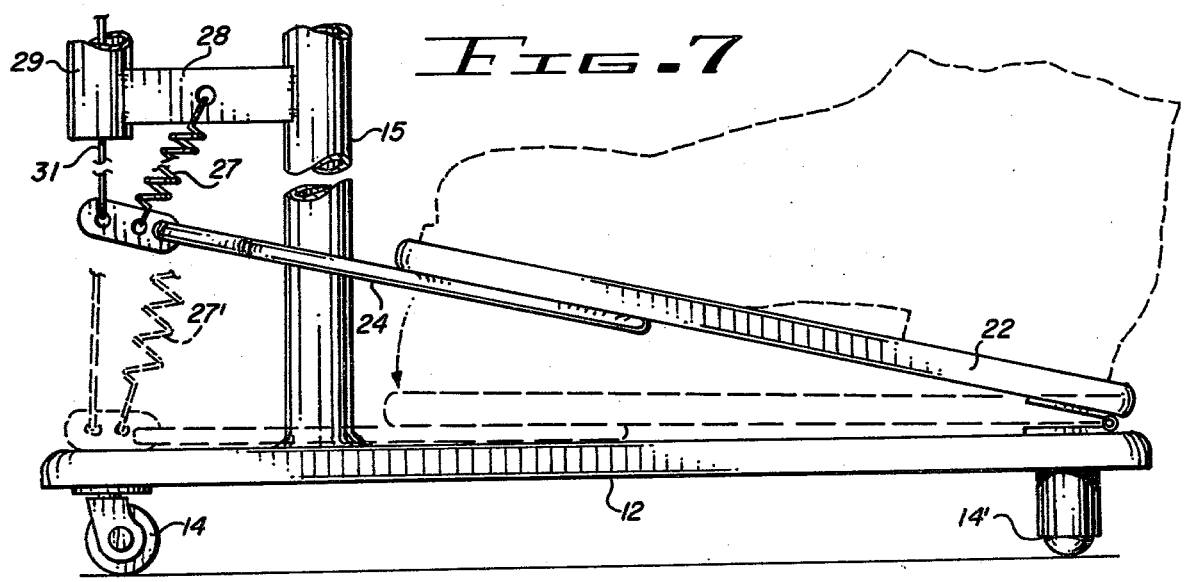

APPARATUS FOR FEEDING ANESTHETIC AND/OR LIFE SUSTAINING GASES DURING A SURGICAL PROCEDURE

BACKGROUND OF THE INVENTION

This invention is directed to apparatus for feeding gases to a patient during a surgical procedure.

A significant factor in the effectiveness and cost to the patient of an operation is the amount of technical help needed in the operating procedure. The doctor, who is performing the anesthesia, i.e. the anesthetist, is utilizing a hand operated bellows type device for feeding gases to the patient in order to produce and maintain general anesthesia during the surgical procedure. This device requires periodic hand maneuvering, which is keeping at times the anesthetist from performing other necessary and sometimes very urgent functions in the course of the surgical procedure.

In the interest of efficiency and economy it is therefore desirable that an implement be provided the anesthetist for controlling the feeding of gases to a patient that can be foot or mechanically operable, thereby permitting him to perform other duties safely and efficiently at the same time he is controlling the procedure of anesthesia.

SUMMARY OF THE INVENTION

In accordance with the invention claimed, an improved bellows type device and associated control equipment is provided for controlling the flow of gases during a surgical procedure.

It is, therefore, one object of this invention to provide an improved gas flow controlling apparatus for use by an anesthetist during a surgical procedure.

Another object of the invention is to provide an improved bellows type device for controlling the flow of a gas to a patient during a surgical procedure which is foot or motor controlled.

A further object of this invention is to provide an improved bellows type device for controlling the flow of a gas to a patient during a surgical procedure which is self contained and motor controlled.

Other objects and advantages of this invention will become apparent as the description proceeds and the features of novelty will be pointed out with particularity in the claims annexed to and forming a part of this specification.

BRIEF DESCRIPTION OF THE DRAWINGS

FIG. 1 is a perspective view of a foot controlled bellows operable gas feeding means for anesthetist's use during a surgical procedure and embodying the invention;

FIG. 2 is a partial perspective view of the bellows actuating means shown in FIG. 1 illustrating the other side of the structure;

FIG. 3 is a top view of FIG. 1 with the bellows removed;

FIG. 4 is a cross-sectional view of FIG. 2 taken along the line 4—4;

FIG. 5 is an enlarged partial back view of the bellows portion of the structure shown in FIG. 1;

FIG. 6 is an enlarged partial front view of the bellows portion of the structure shown in FIG. 1;

FIG. 7 is an enlargement of the foot control shown in FIG. 1; and

FIG. 8 is a partial view of a modification of the structure shown in FIGS. 1-4 illustrating a foot controlled self-contained motor operable bellow gas feeding anesthetic's device.

DESCRIPTION OF THE PREFERRED EMBODIMENT

Referring more particularly to the drawing by characters of reference, FIGS. 1-6 disclose a foot controlled bellows operable gas feeding device or apparatus 10 for use by anesthetists during a surgical procedure. The apparatus comprises a stand 11 having a platform 12 supported on a horizontal surface or floor 13 by a plurality of casters 14, 14' which render the apparatus easily mobile in an operating room. Vertically supported on platform 12 is a shaft or rod 15 which supports at its upper end 16 a bellow actuating or squeezing means 17 for closely embracing a bellows 18 mounted between its relatively movable arms 19 and 20. This squeezing means closely embraces bellows 18 to press or yieldingly exert pressure on the bellows in a controlled manner by the foot of an anesthetist through a suitable foot control means 21.

As shown in FIGS. 1-6, the foot control means 21 comprises a pedal 22 pivotally mounted at its one end 22' to platform 12 of the stand 11 and provided at its other end 23 with a bracket comprising a pair of tubular metallic arms 24 and 25 spacedly positioned at a common end to end 23 of the pedal and bent to engage each other at their other common ends 26. The bracket at the common ends 26 of arms 24 and 25 is provided with a suitable spring means such as coil spring 27 which has one of its ends connected adjacent to the common ends 26 of arms 24 and 25 and its other end connected to an arm 28 mounted to extend laterally from shaft 15.

FIG. 1 shows a hollow shaft 29 extending along at least a part of its length parallel to shaft 15 and tapering at its upper end 30 to engage and to be suitably secured to the upper end 16 of shaft 15. The hollow interior of this shaft 29 forms a passageway for a flexible cord or cable 31 which has one end connected to the common end 26 of arms 24 and 25 and its other end connected through a pair of spaced Y-shaped legs 31A and 31B to the movable arm 20 of the bellow squeezing means 17.

As noted from FIG. 2, the legs 31A and 31B of cord 31 are fed across a pair of guiding rollers 32 through a pair of spaced apertures 33 in arm 19 of the bellow squeezing means 17 to arm 20 where they are suitably attached thereto.

FIGS. 1, 2, 4, 5 and 6 illustrate the manner in which the arm 20 of the bellows squeezing means 17 may be pivotally attached to the upper end 16 of shaft 15 and to arm 19. As shown, arm 19 is provided with a flange 34 at its lower end 19' which supports and has extending laterally outwardly therefrom a pair of spacedly mounted pins 35. These pins extend through a pair of spacedly positioned apertures 36 in the lower common end 20' of arm 20 and merely serve as a support and guiding means for arm 20. This lower end 20' of arm 20 is provided with a pair of spacedly positioned resilient spring means such as the U-shaped metal bands 37 which are spacedly fastened at one common end 38 to the lower end 20' of arm 20 and at their other common end 39 to the lower end 19' of arm 19. Bands 37 are resilient and return to their unbiased initial or normal conditions each time they are biased by foot action of pedal 22.

Bellows 18 comprises the normal pliable elongated gas expandable bag well known in the trade, the interior of which is connected at one point on the bag through a conduit 40 to a source of gas under pressure and through another pressure controllable conduit 41 to a patient under a surgical procedure.

This bellows is positioned between the arms 19 and 20 of the squeezing means 17 as shown in FIG. 1 with the conduit 40 extending outwardly thereof from the lower end thereof between arms 19 and 20. The neck end 18A of the bellows 18 is detachably held to the upper end of the relatively stationary arm 19 of the squeezing means 17 by a clamp 42.

Thus, as the pedal 22 is operated by the foot of an anesthetist, the bellows 18 may be squeezed in the usual manner to control the flow of gas to a patient under surgical procedure.

FIG. 7 illustrates the pedal arrangement shown in FIG. 1 wherein the extended position of spring 27 is represented as spring 27' which under tension returns pedal 22 to its full line position after a foot operation.

To eliminate the fatigue of the anesthetist and to eliminate his foot action of the bellows, pedal 22 may be operated by a direct current motor 43 as shown in FIG. 8 through an arm 44 connected to an offset from the motor shaft 45. A batter pack 46 may be mounted on shaft 15 making the apparatus self contained, if so desired.

Although but two embodiments of the invention have been shown and described, it should be apparent to those skilled in the art that various changes and modifications may be made therein without departing from the spirit of the invention or from the scope of the appended claims.

What is claimed is:

1. An apparatus for feeding life sustaining gases to a patient during a surgical procedure comprising:
    a platform for resting on a supporting surface,
    a shaft mounted on said platform and extending laterally therefrom,
    a bellows,
    a supporting means mounted on one end of said shaft for holding a bellows,
    said supporting means comprising a pair of relatively movable arms hingedly connected at a common end thereof, one of said arms being stationary to said shaft, the other of said arms being movable with respect to said one of said means,
    said bellows being positioned between said arms and having means connectable at one point to a source of gas under pressure and having an outlet at another point for supplying gas under pressure,
    pedal means hingedly mounted at one end thereof on said platform,
    spring means connected to the free end of said pedal means for biasing said pedal means away from said platform, and
    cord means connected to the free end of said pedal means at one end and to the free end of said other of said arms for pivotally moving said other of said arms relative to said one of said arms to selectively compress said bellows and to remove said pressure thereon upon pivotal movement of said pedal means.

2. The apparatus set forth in claim 1 wherein:
    the hinge connection of said relatively movable arms comprises a U-shaped resilient member fastened at different ends to each of said relatively movable arms, and
    an aperture in said other movable arm adjacent the hinged end thereof,
    a pin mounted on the hinged end of said one of said relatively movable arms and extending through said aperture in the other of said arms for guiding the movement of said other of said arms relative to said bellows.

3. The apparatus set forth in claim 2 in further combination with:
    guide rollers spacedly mounted on the free end of said one of said relatively movable arms, and
    said one of said relatively movable arms being provided with apertures adjacent each of said guide rollers,
    said cord means being provided with portions extending over each of said rollers and through said apertures for attachment at spacedly positioned points on the free end of said other of said relatively movable arms.

4. The apparatus set forth in claim 3 in further combination with:
    a direct current motor mounted on said platform for actuating said pedal means, and
    a battery mounted on said platform for actuating said motor.

5. The apparatus set forth in claim 1 in further combination with:
    motor means mounted on said apparatus for pivotally moving said pedal means.

6. The apparatus set forth in claim 5 wherein:
    said motor means comprises a direct current motor, and
    a battery mounted on said platform for furnishing the electrical power for actuating said direct current motor.

* * * * *